US010449131B2

(12) United States Patent
Li et al.

(10) Patent No.: US 10,449,131 B2
(45) Date of Patent: *Oct. 22, 2019

(54) COMPOSITIONS COMPRISING AN EFFICIENT PERFUME BLOOM

(71) Applicant: The Procter & Gamble Company, Cincinnati, OH (US)

(72) Inventors: Jianjun Justin Li, West Chester, OH (US); Eric Scott Johnson, Hamilton, OH (US); Mark Anthony Brown, Union, KY (US); Zerlina Guzdar Dubois, Mason, OH (US); Virginia Tzung-Hwei Hutchins, Cincinnati, OH (US); Kevin Max Labitzke, Hamilton, OH (US); Christa Sue Pelfrey, Colerain Township, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 12 days.

This patent is subject to a terminal disclaimer.

(21) Appl. No.: 15/866,724

(22) Filed: Jan. 10, 2018

(65) Prior Publication Data

US 2018/0193241 A1 Jul. 12, 2018

Related U.S. Application Data

(63) Continuation of application No. 15/151,810, filed on May 11, 2016, now abandoned, which is a continuation of application No. 14/884,053, filed on Oct. 15, 2015, now Pat. No. 9,364,409, which is a continuation of application No. 13/478,415, filed on May 23, 2012, now abandoned.

(60) Provisional application No. 61/490,255, filed on May 26, 2011.

(51) Int. Cl.
| | |
|---|---|
| C11D 3/50 | (2006.01) |
| A61K 8/31 | (2006.01) |
| A61K 8/33 | (2006.01) |
| A61K 8/34 | (2006.01) |
| A61K 8/35 | (2006.01) |
| A61K 8/37 | (2006.01) |
| A61K 8/49 | (2006.01) |
| A61Q 5/02 | (2006.01) |
| A61Q 13/00 | (2006.01) |
| A61Q 19/10 | (2006.01) |
| A61K 8/46 | (2006.01) |
| A61K 8/36 | (2006.01) |
| A61K 8/41 | (2006.01) |
| A61K 8/73 | (2006.01) |
| A61K 8/891 | (2006.01) |
| A61K 8/92 | (2006.01) |

(52) U.S. Cl.
CPC ............ *A61K 8/31* (2013.01); *A61K 8/33* (2013.01); *A61K 8/34* (2013.01); *A61K 8/347* (2013.01); *A61K 8/35* (2013.01); *A61K 8/36* (2013.01); *A61K 8/37* (2013.01); *A61K 8/416* (2013.01); *A61K 8/463* (2013.01); *A61K 8/492* (2013.01); *A61K 8/498* (2013.01); *A61K 8/4926* (2013.01); *A61K 8/4973* (2013.01); *A61K 8/737* (2013.01); *A61K 8/891* (2013.01); *A61K 8/922* (2013.01); *A61Q 5/02* (2013.01); *A61Q 13/00* (2013.01); *A61Q 19/10* (2013.01); *A61K 2800/592* (2013.01)

(58) Field of Classification Search
CPC ........ A61K 2300/00; A61K 8/33; A61K 8/31; A61K 8/34; A61K 8/347
See application file for complete search history.

(56) References Cited

U.S. PATENT DOCUMENTS

| | | |
|---|---|---|
| 5,998,382 A | 12/1999 | Furth et al. |
| 6,806,249 B2 | 10/2004 | Yang et al. |
| 6,858,574 B2 | 2/2005 | Yang et al. |
| 6,995,122 B2 | 2/2006 | Popplewell et al. |
| 7,167,815 B2 | 1/2007 | Labreche et al. |
| H002215 H | 4/2008 | Allen et al. |
| 7,446,079 B2 | 11/2008 | Fadel et al. |
| 7,517,840 B2 | 4/2009 | Fadel et al. |
| 7,648,955 B2 | 1/2010 | Dubois et al. |
| 8,252,356 B2 | 8/2012 | Ogura et al. |
| 9,364,409 B2 * | 6/2016 | Li .................... A61K 8/33 |
| 2002/0049150 A1 | 4/2002 | Miracle et al. |
| 2004/0037792 A1 | 2/2004 | Hiramoto et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |

(Continued)

FOREIGN PATENT DOCUMENTS

| | | |
|---|---|---|
| DE | 102007055124 | 5/2009 |
| WO | WO0067718 A1 | 11/2000 |

(Continued)

OTHER PUBLICATIONS

All final and non-final office actions for U.S. Appl. No. 13/478,415.

(Continued)

*Primary Examiner* — John R Hardee
(74) *Attorney, Agent, or Firm* — Angela K. Haughey

(57) ABSTRACT

The present invention provides personal care compositions having efficient perfume blooms or bursts. The personal care compositions include shampoo and body wash compositions, and comprise perfume materials having high perceived odor intensity at low concentrations of perfume materials.

20 Claims, No Drawings

(56) References Cited

U.S. PATENT DOCUMENTS

| | | |
|---|---|---|
| 2007/0071780 A1 | 3/2007 | Dubois et al. |
| 2007/0117729 A1 | 5/2007 | Taylor et al. |
| 2007/0248553 A1 | 10/2007 | Scavone et al. |
| 2008/0040082 A1 | 2/2008 | Stanton et al. |
| 2008/0070825 A1 | 3/2008 | Bertram et al. |
| 2008/0213451 A1 | 9/2008 | Ogura et al. |
| 2008/0233056 A1 | 9/2008 | Berl |
| 2009/0029900 A1 | 1/2009 | Cetti et al. |
| 2009/0192174 A1 | 7/2009 | Kato et al. |
| 2009/0275494 A1 | 11/2009 | Ferguson et al. |
| 2010/0088847 A1 | 4/2010 | Hicks et al. |
| 2010/0111889 A1* | 5/2010 | Marsh ............... A61K 8/0208 424/76.1 |
| 2010/0119679 A1 | 5/2010 | Dihora et al. |
| 2010/0168253 A1 | 7/2010 | Shoji et al. |
| 2011/0093246 A1 | 4/2011 | Stanton et al. |
| 2011/0241908 A1 | 10/2011 | Han et al. |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0125082 A1 | 5/2012 | Sugiyama et al. |
| 2012/0245075 A1 | 9/2012 | Young et al. |
| 2012/0276175 A1 | 11/2012 | Dihora et al. |
| 2012/0276210 A1 | 11/2012 | Dihora et al. |
| 2012/0282309 A1 | 11/2012 | Dihora et al. |
| 2012/0322709 A1 | 12/2012 | Li et al. |
| 2013/0030944 A1 | 1/2013 | Nicod et al. |
| 2013/0030951 A1 | 1/2013 | Nicod et al. |
| 2013/0103703 A1 | 4/2013 | Han et al. |
| 2013/0303434 A1 | 11/2013 | Young et al. |
| 2014/0064713 A1 | 3/2014 | Niemiec et al. |
| 2015/0170026 A1 | 6/2015 | Jacquot et al. |
| 2015/0177202 A1 | 6/2015 | Ozbek et al. |
| 2015/0212661 A1 | 7/2015 | Robberechts et al. |
| 2016/0250115 A1 | 9/2016 | Li et al. |

FOREIGN PATENT DOCUMENTS

| | | |
|---|---|---|
| WO | WO2005047232 A1 | 5/2005 |
| WO | WO2006138726 A2 | 12/2006 |
| WO | WO2008090397 A1 | 7/2008 |

OTHER PUBLICATIONS

All final and non-final office actions for U.S. Appl. No. 14/884,053.
All final and non-final office actions for U.S. Appl. No. 15/151,810.
PCT International Search Report and Written Opinion for PCT/US2012/039032 dated Nov. 28, 2012.

* cited by examiner

COMPOSITIONS COMPRISING AN EFFICIENT PERFUME BLOOM

This is a continuation of US patent application Ser. No. 15/151,810, filed May 11, 2016, now abandoned, which is a continuation of U.S. patent application Ser. No. 14/884,053, filed Oct. 15, 2015, now U.S. Pat. No. 9,364,409, which is a continuation of U.S. patent application Ser. No. 13/478,415, filed May 23, 2012, now abandoned, which claims priority from U.S. Provisional Application 61/490,255, filed May 26, 2011.

FIELD OF THE INVENTION

The present composition relates to personal care compositions suitable for application to the hair or skin. More specifically, the compositions comprise perfume materials having high perceived odor intensity at low concentrations of perfume materials, and thereby provides compositions having efficient perfume blooms or bursts.

BACKGROUND OF THE INVENTION

Consumers desire personal care products, such as shampoos and body washes, having pleasant fragrances. Products having intense perfume blooms or bursts are particularly appealing as they provide a more noticeable sensory impact. Typical personal care products, however, frequently include many perfume materials that do not contribute to the overall perception of the fragrance at a noticeable level. Moreover, typical personal care products require high concentrations of perfume materials in order to provide a high perceived odor intensity. Accordingly, there is a need for personal care compositions such as shampoos and body washes comprising perfume materials that are more efficient, i.e., perfume materials that are capable of providing a high perceived odor intensity when present in a product at low concentration. More particularly, there is a need for personal care compositions such as shampoos and body washes comprising perfume materials that are capable of providing typical perceived odor intensity levels when present in a product at a lower than typical concentration, and for personal care compositions such as shampoos and body washes comprising perfume materials that are capable of providing higher than typical perceived odor intensity levels when present in a product at a typical concentration.

SUMMARY OF THE INVENTION

The disclosure is directed to shampoo compositions comprising about 10 weight % (wt. %) to about 25 wt. %, based on the total weight of the shampoo composition, of anionic surfactants; and about 0.02 wt. % to about 0.3 wt. %, based on the total weight of the shampoo composition, of a perfume accord comprising at least 10 perfume raw materials, wherein the shampoo composition has an odor intensity score (OIS) of at least about 0.2, preferably about 0.2 to about 1.0. The disclosure also is directed to shampoo compositions comprising about 10 wt. % to about 25 wt. %, based on the total weight of the shampoo composition, of anionic surfactants; and about 0.3 wt. % to about 1 wt. %, based on the total weight of the shampoo composition, of a perfume accord comprising at least 10 perfume raw materials, wherein the shampoo composition has an odor intensity score (OIS) of at least about 0.75, preferably about 0.75 to about 3.

The disclosure is further directed to body wash compositions comprising about 3 wt. % to about 15 wt. %, based on the total weight of the body wash composition, of anionic surfactants; and about 0.05 wt. % to about 0.4 wt. %, based on the total weight of the body wash composition, of a perfume accord comprising at least 10 perfume raw materials, wherein the body wash composition has an odor intensity score (OIS) of at least about 0.8, preferably about 0.8 to about 2. The disclosure also is directed to body wash compositions comprising about 3 weight % (wt. %) to about 15 wt. %, based on the total weight of the shampoo composition, of anionic surfactants; and about 0.4 wt. % to about 1.5 wt. %, based on the total weight of the body wash composition, of a perfume accord comprising at least 10 perfume raw materials, wherein the body wash composition has an odor intensity score (OIS) of at least about 1, preferably about 1 to about 11.

DETAILED DESCRIPTION OF THE INVENTION

As used herein, the articles "a", "an", and "the" when used in a claim, are understood to mean one or more of what is claimed or described.

As used herein, the terms "include," "includes," and "including," are meant to be non-limiting.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfume Accords

The compositions disclosed herein comprise a perfume accord and are suitable for application to the hair or skin. The perfume accords demonstrate a high perceived odor intensity (i.e., a strong scent) when present at low concentrations in the compositions, and thereby are capable of efficiently providing scents to the compositions.

The perfume accord is a blend of perfume raw materials and comprises at least 10 perfume raw materials, for example, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, and/or at least 30 perfume raw materials. The more perfume raw materials that make up a perfume accord, the more complex the perfume accord is considered to be. For example, more simple perfume accords comprise a relatively low number of perfume raw materials, such as less than 10, less than 8, and/or less than 5 perfume raw materials. In contrast, more complex perfume accords, such as the perfume accords provided herein, comprise a relatively higher number of perfume raw materials, for example, at least 10, at least 15, at least 20, at least 25, and/or at least 30 perfume raw materials.

The perfume accord is present in the shampoo compositions at low concentration, such as less than 1 wt. %, less than 0.9 wt. %, less than 0.8 wt. %, less than 0.7 wt. %, less than 0.6 wt. %, less than 0.5 wt. %, less than 0.4 wt. %, less than 0.3 wt. %, less than 0.2 wt. %, and/or less than 0.1 wt. % based on the total weight of the composition. In some embodiments the perfume accord is present in the shampoo compositions at a relatively higher concentration, such as about 0.3 wt. % to about 1 wt. %, about 0.4 wt. % to about 1 wt. %, about 0.5 wt. % to about 0.9 wt. %, and/or about 0.6 wt. % to about 0.8 wt. % based on the total weight of the composition. In some embodiments the perfume accord is present in the shampoo compositions at a relatively lower concentration, such as about 0.02 wt. % to about 0.3 wt. %, about 0.05 wt. % to about 0.3 wt. %, about 0.08 wt. % to about 0.25 wt. %, and/or about 0.1 wt. % to about 0.2 wt. % based on the total weight of the composition.

The perfume accord is present in the body wash compositions at low concentration, such as less than 1.5 wt. %, less than 1.2 wt. %, less than 1.0 wt. %, less than 0.9 wt. %, less than 0.8 wt. %, less than 0.7 wt. %, less than 0.6 wt. %, less than 0.5 wt. %, less than 0.4 wt. %, less than 0.3 wt. %, less than 0.2 wt. %, and/or less than 0.1 wt. % based on the total weight of the composition. In some embodiments the perfume accord is present in the body wash compositions at a relatively higher concentration, such as about 0.4 wt. % to about 1.5 wt. %, about 0.5 wt. % to about 1.5 wt. %, about 0.6 wt. % to about 1.5 wt. %, about 0.7 wt. % to about 1.4 wt. %, about 0.8 wt. % to about 1.3 wt. %, and/or about 0.9 wt. % to about 1.2 wt. % based on the total weight of the composition. In some embodiments the perfume accord is present in the body wash compositions at a relatively lower concentration, such as about 0.05 wt. % to about 0.4 wt. %, about 0.1 wt. % to about 0.4 wt. %, about 0.2 wt. % to about 0.35 wt. %, and/or about 0.2 wt. % to about 0.3 wt. % based on the total weight of the composition.

The perfume accord disclosed herein is not encapsulated. In some embodiments, the compositions comprise perfume materials in addition to the perfume accord, and these additional perfume materials can be encapsulated. A wide variety of capsules exist which will allow for delivery of perfume effect at various times. Examples of such capsules with different encapsulated materials are capsules provided by microencapsulation. One method comprises a capsule core which is coated completely with a material which may be polymeric. See, U.S. Pat. No. 4,145,184 and U.S. Pat. No. 4,234,627.

A wide variety of chemicals are known for fragrance (i.e., perfume) uses, including materials such as aldehydes, ketones and esters. More commonly, naturally occurring plant and animal oils and exudates comprising complex mixtures of various chemical components are known for use as fragrances. The fragrances herein can be relatively simple in their compositions, comprising a single chemical, or can comprise highly sophisticated complex mixtures of natural and synthetic chemical components, all chosen to provide any desired odor.

Preferably the perfume raw materials of the present compositions will have boiling points (BP) of about 500° C. or lower, more preferably about 400° C. or lower, even more preferably about 350° C. or lower. The BP of many perfume raw materials are given in Perfume and Flavor Chemicals (Aroma Chemicals), Steffen Arctander (1969). The C log P value of the perfume raw materials useful herein is preferably greater than about 0.1, more preferably greater than about 0.5, even more preferably greater than about 1.0, even more preferably still greater than about 1.2.

Suitable perfume raw materials include, but are not limited to, ethyl 2,4 decadienoate, allyl heptoate, amyl acetate, ethyl butyrate, Grapefruit Zest (C&A), prenyl acetate, pinoacetaldehyde, 2,6-nonadienol, 3,6-nonadienol, cis-6-nonenol, excital, ebanol, polysantol, orange juice carbonyls, lemon juice carbonyls, orange sinensal, paradiff, tangerinal, benzaldehyde, mandarin aldehyde, undecalactone, norlimbanol, decyl aldehyde, trans-2-hexenal, trans-2-decenal, damascenone, 2-isobutylthiazole, 4-methyl-4-mercaptopentan-2-one, corps cassis 0.1% TEC, patchouli, 2-methoxy-4-vinylphenol, pyridine acetyl 10%, sulfurol, diacetyl, furaneol, maple lactone, allyl amyl glycolate, Ambroxan, alpha damascone damascene, Cetalox, cyclal C, Cedramber, cyclo galbanate, Galbex, Cymal, nerol, Florhydral, P.t. bucinal, iso cyclo citral, Fructone, methyl iso butenyl tetrahydro pyran, Frutene, Delphone, ethyl methyl phenyl glycidate, Violiff, for acetate, Delta damascone damascene, Ambrox, Calone, iso eugenol, Hivernal, methyl beta napthyl ketone, Ozonil, benzyl salicylate, Spirogalbone, cinnamic alcohol, Javanol, dihydro iso jasmonate, Adoxal, Kharismal, pyrazines, ethyl anthranilate, aldehyde supra, Bacdanol, Anethol, irisantheme, yara yara, Keone, cis 3 hexenyl salicylate, methyl nonyl ketone, coumarin, gamma dodecalactone, Applinate, eucalyptol, intreleven aldehyde, heliotropin, indol, Manzanate, ionone, alpha, trans 4 decenal, ionone beta, Oxane, neobutanone, Clonal, methyl octine carbonate, Floralozone, methyl heptine carbonate, methyl nonyl acetaldehyde, Cashmeran, phenoxy ethyl iso butyrate, phenyl acetaldehyde, ethyl methyl phenyl glycidate, undecyl aldehyde, Aurantiol, nectaryl, buccoxime, Laurie aldehyde, nirvanol, Trifernal, pyrazobutyle, Veloutone, Anisic aldehyde, paramenthene, isovaleric aldehyde 0.1% DPG, liminal, labienoxime, rhubofix, iso propyl quinoline, 4-(2,6,6-Trimethyl-1-cyclohexenyl)-3-butenone-2; (3aR-(3aalpha,5abeta,9aalpha,9bbeta))-dodecahydro-3a,6,6,9a-tetramethyl naphtha(2,1-b)furan; 2,6-Dimethyl-5-heptenal; 3,7-Dimethyl-1,6-octadien-3-ol; 3-Methyl-2-buten-1-yl acetate; 3,7-Dimethyl-2,6-octadienenitrile; 2,4-Dimethylcyclohexene-3-carbaldehyde; Phenyl Acetaldehyde, Indol, ethyl methyl dioxolane acetate; 4-(2,6,6-Trimethyl-1,3-cyclohexadienyl)-3-buten-4-one; Cis 3 Hexenyl Acetate; Lauric Ald, Tricyclo decenyl acetate, Para cresyl methyl ether, 7-acetyl, 1,2,3,4,5,6,7,8-octahydro-1,1,6,7-tetramethyl naphthalene; 3-buten-2-one; 3-methyl-4-(2,6,6-trimethyl-2-cyclohexen-1-yl); Acetic acid (Cyclohexyloxy), 2-propenyl ester; 3-buten-2-one, 4-(2,6,6-trimethyl-2-cyclohexen-1-yl), (E); Decyl Aldehyde, Methyl-3,4-dioxy(cylcoacetonyl) benzene; 2,6-Dimethyl-2,6-octadien-8-ol; ortho tertiary butyl cyclohexanyl acetate; Hexanoic acid, 2-propenyl ester; 4-Methoxybenzaldehyde; 3-(3-Isopropylphenyl)butanal; Iso 2-Methoxy-4-(2-propenyl)phenol, Tetra Hydro 3,7-Dimethyl-1,6-octadien-3-ol; 1-methyl-4-isopropenyl-1-cyclohexene; Methyl phenyl carbonyl acetate; Hexahydro-4,7methano-1H-inden-5(or 6)-yl propionate; Benzaldehyde, 3,7-Dimethyl-2,6-octadienal; 3,3-Dimethyl-5-(2,2,3-trimethyl-3-cycloenten-1-yl)-4-penten-2-ol; 2-Methoxy-4-(2-propenyl)phenol; 3,7-dimethyl-6-octen-1-ol; Allyl heptanoate; 1,3-Oxathiane, 2-methyl-4-propyl-, cis-; paradiff; (all-E)-alpha-sinensal, 2,6,10-trimethyl-2(E),6(E),9(E),11-dodecatetraenal; mandarin aldehyde, p-I-menthen-8 thiol; 4-Methyl-3-decen-5-ol; Ethyl caproate, Ethyl-2-4-decadienoate, 4-Penten-1-one, 1-(5,5-Dimethyl-1-cyclohexen-1-yl)-; 1H-Indene-a-propanal, 2,3-dihydro-1,1-dimethyl-(9CI); Methyl nonyl acetaldehyde; Orange juice Carbonyls; 4 dodecenal; 3-cyclohexene-1-carboxaldehyde, 2,4-dimethyl; 2,6,-nonenol; 2,6-nonadeinal; 2,6-nonadienol; 3-P-cumenyl-propionaldehyde 4-(1-methylethyl)-benzenepropanal; 1-(2,6,6-Trimethyl-1,3-cyclohexandienyl)-2-buten-1-one; 6-(Z,3-pentenyl)-tetrahydro-(2H)-pyranone-2; 3-Methyl-(cis-2-penten-1-yl)-2-cyclopenten-1-one. 2,6 nonenol; 2,6-nonadienol; (3aR-(3aalpha,5abeta,9aalpha,9bbeta))-dodecahydro-3a,6,6,9a-tetramethyl naphtha(2,1-b)furan; Beta Gamma Hexenol; Cis 3 Hexenyl Acetate; 3-P-cumenyl-propionaldehyde 4-(1-methylethyl)-benzenepropanal; 1-(2,6,6-Trimethyl-1,3-cyclohexandienyl)-2-buten-1-one; 3-(3-Isopropylphenyl)butanal; 4-Penten-1-one, 1-(5,5-Dimethyl-1-cyclohexen-1-yl)-; 1H-Indene-a-propanal, 2,3-dihydro-1,1-dimethyl-(9CI); 4-(2,6,6-Trimethyl-1-cyclohexenyl)-3-butenone-2; 6-(Z,3-pentenyl)-tetrahydro-(2H)-pyranone-2; 2,6-Dimethyl-5-heptenal; 6,6-Dimethylbicyclo{3.1.1)Hept-2-ene-2-proponal; 3-cyclohexene-1-carboxaldehyde, 2,4-dimethyl; 4-Methyl-3-decen-5-ol; ortho tertiary butyl cyclohexanyl acetate; 3-Methyl-(cis-2-penten-1-yl)-2-cyclopenten-1-one; 4-Pentene-2-ol, 3,3-dimethyl-5-(2,2,3-trimethyl-3-cyclopenten-1-yl)-. Benzaldehyde; Undeclactone; 4-(2,6,6-Trimethyl-1-cyclohexenyl)-3-butenone-2; Allyl Heptanoate; 1,3-Oxathiane, 2-methyl-4-propyl-, cis-; Paradiff, (all-E)-alpha-sinensal, 2,6,10-trimethyl-2(E),6(E),9(E),11-dodecatetraenal; mandarin aldehyde; 4-dodecenal; p-1-menthen-8 thiol; Orange Juice Carbonyls; Decyl Aldehyde; 4-Methyl-3-decen-5-ol; 4-Penten-1-one, 1-(5,5-Dimethyl-1-cyclohexen-1-yl)-. Hexanoic acid, 2-propenyl ester; 4-Methoxybenzaldehyde; Allyl Heptanoate; Benzaldehyde; 1,3-Oxathiane, 2-methyl-4-propyl-, cis-; Decyl Aldehyde; Ethyl 2'4-decadienoate; Ethyl Caproate; 4-Penten-1-one, 1-(5,5-Dimethyl-1-cyclohexen-1-yl)-; p-1-menthen-8 thiol; (all-E)-alpha-sinensal 2,6,10-trimethyl-2(E),6(E),9(E),11-dodecatetraenal; IH-Indene-a-propanal, 2,3-dihydro-1,1-dimethyl-(9C1); 4-(2,6,6-Trimethyl-1-cyclohexenyl)-3-butenone-2; 3 dodecenal; Methyl Nonyl Acetaldehyde; Orange Juice Carbonyls; Paradiff; 4 dodecenal; 3-cyclohexene-1-carboxaldehyde, 2,4-dimethyl; 4-Methyl-3-decen-5-ol; animal fragrances such as musk oil, civet, castoreum, ambergris; plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, acetophenone, adoxal, aldehyde C-12, aldehyde C-14, aldehyde C-18, allyl caprylate, allyl heptanoate, ambroxan, dimethylindane derivatives, anethole, anisaldehyde, benzaldehyde, benzyl acetate, benzyl alcohol and ester derivatives, benzyl propionate, benzyl salicylate, beta gamma hexanol, borneol, butyl acetate, camphor, carbitol, carvone, cetalox, cinnamaldehyde, cinnamyl acetate, cinnamyl alcohol, cis-3-hexanol and ester derivatives, cis-3-hexenyl methyl carbonate, cis jasmone, citral, citronnellol and ester derivatives, cumin aldehyde, cyclamen aldehyde, cyclo galbanate, damascones, decanol, decyl aldehyde, estragole, delta muscenone, dihydromyrcenol, dimethyl benzyl carbinol, 6,8-dimethyl-2-nonanol, dimethyl benzyl carbinyl butyrate, ethyl isobutyrate, ethyl propionate, ethyl caprylate, ethyl cinnamate, ethyl hexanoate, ethyl valerate, exaltolide, fenchone, galaxolide, geraniol and ester derivatives, hedione, helional, 2-heptonone, hexenol, hexyl salicylate, hydroxycitrolnellal, ionones, isoeugenol, isoamyl iso-valerate, iso E super, linalool acteate, lilial, lyral, majantol, mayol, menthol, p-methylacetophenone, methyl cedrylone, methyl dihydrojasmonate, methyl eugenol, mugetanol, para hydroxy phenyl butanone, phenoxynol, phenyl-acetaldehyde dimethyl acetate, phenoxyethyl isobutyrate, phenyl ethyl alcohol, pinenes, sandalore, sanjinol, santalol, thymol, terpenes, tonalide, 3,3,5-trimethylcyclohexanol, undecylenic aldehyde, phenyl ethyl alcohol, linalool, geraniol, citronellol, cinnamic alcohol, iso bornyl acetate, benzyl acetate, para-tertiary-butyl cyclohexyl acetate, linalyl acetate, dihydro-nor-dicyclopentadienyl acetate, dihydro-nor-dicyclopentadienyl propionate, amyl salicylate, benzyl salicylate, para-iso-propyl alpha-octyl hydrocinnamic aldehyde, hexyl cinnamic aldehyde, hydroxy citronellal, heliotropin, anisaldehyde, citral, dextro limonene, coumarin, ionone gamma methyl, methyl beta naphthyl ketone, gamma undecalactone, eugenol, musk xylol, 1,3,4,6,7,8-hexahydro-4,6,6,7,8,8-hexamethylcyclopenta-gamma-2-benzopyrane, 4-acetyl-6-tertiarybutyl-1,1-dimethyl indan, 6-acetyl-1,1,3,4,4,6-hexamethyl tetrahydro naphthalene, beta naphthyl ethyl ether, methyl eugenol, methyl cedrenyl ketone, patchouli, lavandin, geranyl nitrile, alpha ionone, alpha beta ionone, benzyl iso eugenol, amyl cinnamic aldehyde, beta gamma hexenol, orange CP, ortho-tertiary-butyl cyclohexyl acetate, 2-methyl-3-(para-iso-propylphenyl)propionaldehyde, trichloro methyl phenyl carbinyl acetate, nonane diol-1,3-acetate, methyl dihydro jasmonate, phenoxy ethyl iso butyrate, citronella, citronellal, citrathal, tetrahydromuguol, ethylene brassylate, musk ketone, musk tibetine, phenyl ethyl acetate, oakmoss 25%, hexyl salicylate, eucalyptol, Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl)pent-4-en-2-ol (Ebanol), Phenethyl isobutyrate, Florhydral, phenyl ethyl alcohol, bourgeonal, gamma-Undecalactone_(racemic), Dihydromyrcenol, Ethyl_2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Other suitable perfume raw materials can be found in the following U.S. Pat. Nos. 4,145,184; 4,209,417; 4,515,705; and 4,152,272, which are incorporated herein by reference in their entireties.

Suitable perfume raw materials include the following: Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl) pent-4-en-2-ol (Ebanol), Phenethyl isobutyrate, Florhydral, phenyl ethyl alcohol, bourgeonal, gamma-Undecalactone_ (racemic), Dihydromyrcenol, Ethyl_2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additional suitable perfume raw materials include the following: Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Further suitable perfume raw materials include the following: Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additionally, suitable perfume raw materials include the following: 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

One example of a perfume accord comprises ligustral or triplal, cis-3-hexenyl acetate, delta damascene, cyclemax, ethyl-2-methyl butyrate, hexyl acetate, allyl cyclohexane propionate, ethyl linalool, undecalactone, ambroxan, florhydral, ethyl-2-methyl pentanoate, prenyl acetate, ethyl maltol, methyl iso-butenyl tetrahydropyran, ethyl oenanthate, oxane, allyl heptoate, frutene, and ionone gamma methyl.

Another example of a perfume accord comprises octyl aldehyde, oxane, pino acetaldehyde, anethol usp, alpha damascene, citronellol, methyl pamplemousse, ambronat, 4-tertiary butyl cyclohexyl acetate, hexyl acetate, cis-3-hexenyl acetate, melonal, irone alpha refined, dimethyl benzyl carbinyl acetate, precyclemone B, frutene, helvetolide 947650, undecalactone, ethyl-2-methyl pentanoate, phenyl acetaldehyde, gamma decalactone, dihydro beta ionone, ethyl-2-methyl butyrate, ethyl methyl phenyl glycidate, romascone, citral, and ethyl vanillin.

Another example of a perfume accord comprises lemon cold-pressed, melonal, para hydroxy phenyl butanone, undecalactone, ligustral or triplal, undecavertol, iso E super or wood, iso eugenol, ambronat, beta gamma hexenol, ethyl maltol, oxane, cis-3-hexenyl acetate, delta damascene, dihydro myrcenol, ethyl caproate, ethyl-2-methyl butyrate, heliotropin, hexyl acetate, ionone gamma methyl, linalool, and linalyl acetate.

Odor Intensity Score (OIS)

The odor intensity score (OIS) of a composition is determined by Formula I:

$$1/n \sum_{i=1}^{n} C_i / M_i = OIS. \qquad \text{Formula (I)}$$

In Formula I, n is the number of perfume raw materials present in the perfume accord, $C_i$ is the concentration of the $i^{th}$ perfume raw material in the composition, and $M_i$ is the concentration of the $i^{th}$ perfume raw material sufficient to provide an odor intensity rating (OIR) in a composition chassis of about 2 on a scale from zero to five. The composition chassis has the same formulation as the composition with the exception that the composition chassis does not include the perfume accord.

The odor intensity rating (OIR) is determined by a sensory panel rating the sensory intensity of a perfume raw material in a composition chassis (i.e., the composition without the perfume accord) on a scale from zero to five. The sensory panel consists of about 15 to about 20 naïve panelists, both male and female, aged 25 to 55. For each perfume raw material, the sensory panel rates at least two samples, one of which includes the perfume raw material at a concentration of about 10-times the odor detection threshold of the perfume raw material, and the other of which includes the perfume raw material at a concentration of about 250-times the odor detection threshold of the perfume raw material. The odor detection threshold of a perfume raw material is the concentration of the perfume raw material at which 50% of the population detects an odor above background. By way of example, if the odor detection threshold of a perfume raw material is 20 ppm, one sample includes the perfume raw material in the composition chassis at about 200 ppm and another sample includes the perfume raw material in the composition chassis at about 5000 ppm. An individual rating by a panel member of zero means that the individual could not detect an odor and an individual rating by a panel member of five means that the individual could detect an extremely strong odor. The ratings of each panel member at each concentration of perfume raw material are summed and divided by the number of members to provide a mean rating that defines the OIR at each concentration tested.

M is determined for each perfume raw material by using the OIR values (obtained as described above) to calculate the concentration of the perfume raw material in the composition chassis sufficient to provide an OIR of about 2. The methods for determining M using a sensory panel include extrapolating or interpolating the OIR values to obtain a value for M. The methods for determining M using a sensory panel also include preparing samples using perfume raw materials at concentrations other than (or in addition to) about 10-times the odor detection threshold of the perfume raw material and about 250-times the odor detection threshold of the perfume raw material.

Without intending to be bound by theory, perfume raw materials having a low value for M typically demonstrate a high perceived odor intensity (i.e., a strong scent) when present in a composition at low concentration. Put another way, a first perfume raw material having a lower relative value for M than a second perfume raw material typically demonstrates a higher perceived odor intensity (i.e., a stronger scent) relative to the perceived odor intensity of the second perfume raw material when the first and second perfume raw materials are present in a composition at the same concentration. Thus, perfume accords having a high number of perfume raw materials with low M values advantageously provide a high perceived odor intensity (i.e., a strong scent) when present in a composition at low concentration. In some embodiments, about 20% to about 100% of the perfume raw materials present in a perfume accord have a value for M of about 1 ppm to about 1000 ppm, for example, about 30% to about 100%, about 40% to about 100%, about 50% to about 100%, about 60% to about 100%, and/or about 70% to about 100% of the perfume raw materials present in the perfume accord. In some embodiments, about 20% to about 100% of the perfume raw materials present in a perfume accord have a value for M of about 1 ppm to about 800 ppm, for example, about 30% to about 100%, about 40% to about 100%, about 50% to about 100%, about 60% to about 100%, and/or about 70% to about 100% of the perfume raw materials present in the perfume accord. In some embodiments, about 20% to about 100% of the perfume raw materials present in a perfume accord have a value for M of about 1 ppm to about 600 ppm, for example, about 30% to about 100%, about 40% to about 100%, about 50% to about 100%, about 60% to about 100%, and/or about 70% to about 100% of the perfume raw materials present in the perfume accord.

The compositions disclosed herein have a high percentage of perfume raw materials that contribute to the overall perception of the fragrance at a noticeable level. Without intending to be bound by theory, perfume raw materials contribute to the overall perception of the fragrance at a noticeable level when the ratio of the concentration of the perfume raw material in a composition to the M value of the perfume raw material in the corresponding composition chassis (i.e., C/M) is high. In some embodiments, $C_i/M_i$ is at least 0.05 for about 75% to about 100% of the perfume raw materials present in the perfume accord, for example, about 80% to about 100%, and/or about 90% to about 100% of the perfume raw materials present in the perfume accord. In some embodiments, $C_i/M_i$ is at least 0.1 for about 70% to about 100% of the perfume raw materials present in the perfume accord, for example, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.2 for about 45% to about 100% of the perfume raw materials present in the perfume accord, for example, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.3 for about 40% to about 100% of the perfume raw materials present in the perfume accord, for example, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.4 for about 35% to about 100% of the perfume raw materials present in the perfume accord, for example, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.5 for about 30% to about 100% of the perfume raw materials present in the perfume accord, for example, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.6 for about 25% to about 100% of the perfume raw materials present in the perfume accord, for example, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.7 for about 20% to about 100% of the perfume raw materials present in the perfume accord, for example, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.8 for about 20% to about 100% of the perfume raw materials present in the perfume accord, for example, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 0.9 for about 20% to about 100% of the perfume raw materials present in the perfume accord, for example, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord. In some embodiments, $C_i/M_i$ is at least 1.0 for about 15% to about 100% of the perfume raw materials present in the perfume accord, for example, about 20% to about 100%, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, and/or about 95% to about 100% of the perfume raw materials present in the perfume accord.

The shampoo compositions disclosed herein have a high OIS value, such as an OIS value of at least about 0.2, at least about 0.3, at least about 0.4, at least about 0.5, at least about 0.6, at least about 0.7, at least about 0.75, at least about 0.8, at least about 0.9, at least about 1.0, at least about 1.2, at least about 1.4, at least about 1.6, at least about 1.8, at least about 2.0, at least about 2.2, at least about 2.4, at least about 2.6, at least about 2.8, and/or at least about 3.0. In some embodiments the shampoo compositions have a relatively higher OIS, such as about 0.75 to about 3, about 0.8 to about 2.8, about 1 to about 2.6, about 1.5 to about 2.4, and/or about 1.8 to about 2.2. In some embodiments the shampoo compositions have a relatively lower OIS, such as about 0.2 to about 1.0, about 0.4 to about 1, about 0.5 to about 0.9 and/or about 0.6 to about 0.8.

The body wash compositions disclosed herein have a high OIS value, such as an OIS value of at least about 0.8, at least about 0.9, at least about 1.0, at least about 1.2, at least about 1.4, at least about 1.6, at least about 1.8, at least about 2.0, at least about 2.2, at least about 2.4, at least about 2.6, at least about 2.8, and/or at least about 3.0, at least about 3.2, at least about 3.4, at least about 3.6, at least about 3.8, at least about 4.0, at least about 4.2, at least about 4.4, at least about 4.6, at least about 4.8, at least about 5.0, at least about 5.5, at least about 6.0, at least about 6.5, at least about 7.0, at least about 7.5, at least about 8.0, at least about 8.5, at least about 9.0, at least about 9.5, at least about 10.0, at least about 10.5, and/or at least about 11.0. In some embodiments the body wash compositions have a relatively higher OIS, such as about 1 to about 11, about 2 to about 10, about 3 to about 9, and/or about 4 to about 8. In some embodiments the body wash compositions have a relatively lower OIS, such as about 0.8 to about 2, about 1 to about 2, about 1.2 to about 2, and/or about 1.5 to about 2.

Compositions

The shampoo and body wash compositions include efficient compositions comprising very low concentrations of perfume accord and efficient compositions comprising very high perceived odor intensity.

A. Efficient Compositions Comprising Very Low Concentrations of Perfume Accord.

The compositions include compositions having a very low concentration of a perfume accord and a high perceived odor intensity.

Such compositions include shampoo compositions having an OIS of at least about 0.2, and comprising about 10 wt. % to about 25 wt. % of anionic surfactants, and about 0.02 wt. % to about 0.3 wt. % of a perfume accord comprising at least 10 perfume raw materials. In some embodiments, the shampoo compositions have an OIS of about 0.2 to about 1.0.

Such compositions also include body wash compositions having an OIS of at least about 0.8, and comprising about 3 wt. % to about 15 wt. % of anionic surfactants, and about 0.05 wt. % to about 0.4 wt. % of a perfume accord comprising at least 10 perfume raw materials. In some embodiments, the body wash compositions have an OIS of about 0.8 to about 2.0.

B. Efficient Compositions Comprising Very High Perceived Odor Intensity.

The compositions include compositions having a low concentration of a perfume accord and a very high perceived odor intensity.

Such compositions include shampoo compositions having an OIS of at least about 0.75, and comprising about 10 wt. % to about 25 wt. % of anionic surfactants, and about 0.3 wt.

% to about 1.0 wt. % of a perfume accord comprising at least 10 perfume raw materials. In some embodiments, the compositions have an OIS of about 0.75 to about 3.0.

Such compositions also include body wash compositions having an OIS of at least about 1, and comprising about 3 wt. % to about 15 wt. % of anionic surfactants, and about 0.4 wt. % to about 1.5 wt. % of a perfume accord comprising at least 10 perfume raw materials. In some embodiments, the compositions have an OIS of about 1 to about 11.0.

C. Anionic Surfactants.

The compositions disclosed herein comprise one or more anionic surfactants.

The anionic surfactants are present in the shampoo compositions an amount of about 10 wt. % to about 25 wt. %, based on the total weight of the shampoo composition, for example, about 12 wt. % to about 20 wt. %, about 14 wt. % to about 18 wt. %, and/or about 15 wt. % to about 16 wt. %.

The anionic surfactants are present in the body wash compositions an amount of about 3 wt. % to about 15 wt. %, based on the total weight of the body wash composition, for example, about 4 wt. % to about 13 wt. %, about 5 wt. % to about 11 wt. %, and/or about 7 wt. % to about 9 wt. %.

Suitable anionic surfactants include, but are not limited to, anionic surfactants are selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium trideceth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, branched and non-branched versions of decyl and undecyl alkyl sulfates which are either ethoxylated or non-ethoxylated; decyl alcohol modified lauryl sulfate; paraffin sulfonates with chain lengths ranging from C13 to C17; mixtures of linear and branched-chain alcohol sulfates with carbon chain lengths C12 to C17 which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates, and mixtures thereof.

Shampoo Formulations

The compositions disclosed herein include shampoo compositions. Shampoo compositions include a detersive surfactant, a carrier, optional anti-dandruff actives, and other optional components.

A. Detersive Surfactant

Shampoo compositions include a detersive surfactant. The detersive surfactant provides cleaning performance to the composition. The detersive surfactant in turn comprises anionic detersive surfactants, zwitterionic or amphoteric detersive surfactants, or combinations thereof. Various examples and descriptions of detersive surfactants are set forth in U.S. Pat. No. 6,649,155; U.S. Patent Publication 2008/0317698; and U.S. Patent Publication 2008/0206355, and are incorporated herein by reference.

The concentration of the anionic surfactant component in a shampoo should be sufficient to provide the desired cleaning and lather performance, and generally ranges from about 10 wt. % to about 25 wt. %, about 12 wt. % to about 20 wt. %, about 14 wt. % to about 18 wt. %, and/or about 15 wt. % to about 16 wt. %.

Anionic surfactants suitable for use in shampoo compositions include alkyl and alkyl ether sulfates. Other suitable anionic detersive surfactants include the water-soluble salts of organic, sulfuric acid reaction products. Still other suitable anionic detersive surfactants include the reaction products of fatty acids esterified with isethionic acid and neutralized with sodium hydroxide. Other similar anionic surfactants are described in U.S. Pat. Nos. 2,486,921; 2,486,922; and 2,396,278.

Anionic detersive surfactants for use in shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium trideceth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, branched and non-branched versions of decyl and undecyl alkyl sulfates which are either ethoxylated or non-ethoxylated; decyl alcohol modified lauryl sulfate; paraffin sulfonates with chain lengths ranging from C13 to C17; mixtures of linear and branched-chain alcohol sulfates with carbon chain lengths C12 to C17 which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates, and combinations thereof. Suitable anionic surfactants include sodium lauryl sulfate and sodium laureth sulfate.

Suitable amphoteric or zwitterionic detersive surfactants for use in shampoo compositions include those which are known for use in hair care or other personal care cleansing. Concentrations of such amphoteric detersive surfactants range from about 0.5% to about 20%, and from about 1% to about 10%. Non limiting examples of suitable zwitterionic or amphoteric surfactants are described in U.S. Pat. Nos. 5,104,646 and 5,106,609.

Amphoteric detersive surfactants suitable for use in shampoo compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Amphoteric detersive surfactants include cocoamphoacetate, cocoamphodiacetate, lauroamphoacetate, lauroamphodiacetate, and mixtures thereof.

Zwitterionic detersive surfactants include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in shampoo compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

B. Anti-Dandruff Actives

The shampoo compositions of the present composition may also contain an anti-dandruff agent. Suitable, non-limiting examples of anti-dandruff agents include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff agents typically are pyridinethione salts. Such anti-dandruff agents should be physically and chemically compatible with the essential components of the composition, and should not otherwise unduly impair product stability, aesthetics or performance.

Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

In an embodiment the composition may also contain an effective amount of a zinc containing material. Herein "zinc containing material" or ZCM means a material comprising zinc bound covalently, and/or ionically, or physically by a host material. The ZCM may have an aqueous solubility within the composition of less than about 25%, by weight, at 25° C. The ZCM may be present from about 0.001% to about 10%. In a further embodiment, the ZCM may be present from about 0.1% to about 3%. Examples of ZCM which may be useful in certain embodiments include the following: Zinc aluminate, Zinc carbonate, Zinc oxide and materials containing zinc oxide (i.e., calamine), Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide and hydroxy sulfate, zinc-containing layered materials, hydrozincite (zinc carbonate hydroxide), basic zinc carbonate, aurichalcite (zinc copper carbonate hydroxide), rosasite (copper zinc carbonate hydroxide) and combinations thereof.

C. Aqueous Carrier

The shampoo formulations can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present composition includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

D. Other Optional Components

Shampoo compositions may further comprise other optional ingredients that are known for use or otherwise useful in compositions. Such optional ingredients are most typically those described in reference books such as the CTFA Cosmetic Ingredient Handbook, Second Edition, The Cosmetic, Toiletries, and Fragrance Association, Inc. 1988, 1992.

Further non-limiting examples of such optional ingredients include perfumes or fragrances, coloring agents or dyes, hair bleaching agents, thickeners, moisturizers, emollients, pharmaceutical actives, vitamins or nutrients, anti-dandruff agents, perfumes, hair colorants, hair perming agents, hair growth or restorer agents, and similar other materials.

Body Wash Formulations

The compositions disclosed herein include body wash compositions. Body wash compositions include a detersive surfactant, a carrier, and other optional components.

A. Detersive Surfactant

Body wash compositions include a detersive surfactant. The detersive surfactant provides cleaning performance to the composition. The detersive surfactant in turn comprises anionic detersive surfactants, zwitterionic or amphoteric detersive surfactants, or combinations thereof. Various examples and descriptions of detersive surfactants are set forth in U.S. Pat. No. 6,649,155; U.S. Patent Publication 2008/0317698; and U.S. Patent Publication 2008/0206355, and are incorporated herein by reference.

The concentration of the anionic surfactant component in a body wash should be sufficient to provide the desired cleaning and lather performance, and generally ranges from about 3 wt. % to about 15 wt. %, about 4 wt. % to about 13 wt. %, about 5 wt. % to about 11 wt. %, and/or about 7 wt. % to about 9 wt. %.

Anionic surfactants suitable for use in body wash compositions include alkyl and alkyl ether sulfates. Other suitable anionic detersive surfactants include the water-soluble salts of organic, sulfuric acid reaction products. Still other suitable anionic detersive surfactants include the reaction products of fatty acids esterified with isethionic acid and neutralized with sodium hydroxide. Other similar anionic surfactants are described in U.S. Pat. Nos. 2,486,921; 2,486, 922; and 2,396,278.

Anionic detersive surfactants for use in body wash compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium trideceth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, branched and non-branched versions of decyl and undecyl alkyl sulfates which are either ethoxylated or non-ethoxylated; decyl alcohol modified lauryl sulfate; paraffin sulfonates with chain lengths ranging from C13 to C17; mixtures of linear and branched-chain alcohol sulfates with carbon chain lengths C12 to C17 which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates, and combinations thereof. Suitable anionic surfactants include sodium lauryl sulfate and sodium laureth sulfate.

Suitable amphoteric or zwitterionic detersive surfactants for use in body wash compositions include those which are known for use in hair care or other personal care cleansing. Concentrations of such amphoteric detersive surfactants range from about 0.5% to about 20%, and from about 1% to about 10%. Non limiting examples of suitable zwitterionic or amphoteric surfactants are described in U.S. Pat. Nos. 5,104,646 and 5,106,609.

Amphoteric detersive surfactants suitable for use in body wash compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Amphoteric detersive surfactants include cocoamphoacetate, cocoamphodiacetate, lauroamphoacetate, lauroamphodiacetate, and mixtures thereof.

Zwitterionic detersive surfactants include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in body wash compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

B. Aqueous Carrier

The body wash formulations can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present composition includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Other Optional Components

Body wash compositions may further comprise other optional ingredients that are known for use or otherwise useful in compositions. Such optional ingredients are most typically those described in reference books such as the CTFA Cosmetic Ingredient Handbook, Second Edition, The Cosmetic, Toiletries, and Fragrance Association, Inc. 1988, 1992.

Further non-limiting examples of such optional ingredients include perfumes or fragrances, coloring agents or dyes, hair bleaching agents, thickeners, moisturizers, emollients, pharmaceutical actives, vitamins or nutrients, anti-dandruff agents, perfumes, hair colorants, hair perming agents, hair growth or restorer agents, and similar other materials.

EXAMPLES

Example 1

Preparation of Shampoo Compositions

Shampoo compositions I to V were prepared by conventional formulation and mixing techniques. The component amounts provided in Table 1 are percent by weight (wt. %) based on the total weight of the shampoo composition.

TABLE 1

| Ingredient | EXAMPLE SHAMPOO COMPOSITION | | | | |
|---|---|---|---|---|---|
| | I | II | III | IV | V |
| Water | q.s. | q.s. | q.s. | q.s. | q.s. |
| Polyquaterium 76 [1] | 0.25 | — | — | — | — |
| Guar, Hydroxylpropyl Trimonium Chloride [2] | — | 0.25 | 0.25 | — | — |
| Guar, Hydroxylpropyl Trimonium Chloride [3] | — | — | — | 0.25 | — |
| Polyquaterium 6 [4] | — | — | — | — | 0.25 |
| Sodium Laureth Sulfate (SLE3S) [5] | 6 | 6 | 6 | — | 6 |
| Sodium Laureth Sulfate (SLE1S) [6] | — | — | — | 10.5 | — |
| Sodium Lauryl Sulfate (SLS) [7] | 7 | 5 | 6 | 1.5 | 10 |
| Silicone [8] | 0.5 | 1.00 | 1.0 | 1.00 | 1.00 |
| Gel Network [9] | — | — | — | 27.3 | 27.3 |
| Cocoamidopropyl Betaine [10] | 2.0 | 1.0 | 1.0 | 2.00 | — |
| Cocoamide MEA [11] | 0.85 | 0.85 | 0.85 | 0.85 | 1.6 |
| Ethylene Glycol Distearate [12] | 1.50 | 1.50 | 1.50 | 1.50 | 1.50 |
| Sodium Benzoate | 0.25 | 0.25 | 0.25 | 0.25 | 0.25 |
| Disodium EDTA | 0.13 | 0.13 | 0.13 | 0.13 | 0.13 |
| 5-Chloro-2-methyl-4-isothiazolin-3-one, Kathon CG | 0.0005 | 0.0005 | 0.0005 | 0.0005 | 0.0005 |

TABLE 1-continued

| | | | | | |
|---|---|---|---|---|---|
| Sodium Chloride/Ammonium Xylene Sulfonate | Adjust viscosity to 2000 to 10,000 cps | Adjust viscosity to 2000 to 10,000 cps | Adjust viscosity to 2000 to 10,000 cps | Adjust viscosity to 2000 to 10,000 cps | Adjust viscosity to 2000 to 10,000 cps |
| Citric Acid or Sodium Citrate Dihydrate | Adjust to pH 5 to 7 | Adjust to pH 5 to 7 | Adjust to pH 5 to 7 | Adjust to pH 5 to 7 | Adjust to pH 5 to 7 |

[1] Mirapol AT-1, Copolymer of Acrylamide(AM) and TRIQUAT, MW = 1,000,000; CD = 1.6 meq./gram; Supplier Rhodia
[2] Jaguar C500, MW - 500,000, CD = 0.7, supplier Rhodia
[3] Jaguar C17, supplier Rhodia
[4] Mirapol 100S, supplier Rhodia
[5] Sodium Laureth Sulfate, supplier P&G
[6] Sodium Laureth Sulfate, supplier P&G
[7] Sodium Lauryl Sulfate, supplier P&G
[8] Dimethicone Fluid, Viscasil 330M; 30 micron particle size; supplier Momentive Silicones
[9] Gel Networks; See Composition below. The water is heated to about 74° C. and the Cetyl Alcohol, Stearyl Alcohol, and the SLES Surfactant are added to it. After incorporation, this mixture was passed through a heat
exchanger where it was cooled to about 35° C. As a result of this cooling step, the Fatty Alcohols and surfactant crystallized to form a crystalline gel network.

| Ingredient | Wt. % |
|---|---|
| Water | 86.14% |
| Cetyl Alcohol | 3.46% |
| Steary Alcohol | 6.44% |
| Sodium laureth-3 sulfate (28% Active) | 3.93% |
| 5-Chloro-2-methyl-4-isothiazolin-3-one, Kathon CG | 0.03% |

[10] Tegobetaine F-B, supplier Evonik
[11] Monamid CMA, supplier Evonik
[12] Ethylene Glycol Distearate, EGDS Pure, supplier Evonik Example 2

Shampoo Compositions Comprising Comparative Perfume Accords

Comparative perfume compositions were prepared according to the formulations provided in Tables 2 to 4. The amount of perfume raw material provided in the table is a percent by weight (wt. %) based on the total weight of the perfume accord (i.e., the blend of perfume raw materials).

M is the concentration of the perfume raw material sufficient to provide an odor intensity rating (OIR) in shampoo composition I or II of about 2 on a scale from zero to five. C is the concentration of the perfume raw material in the shampoo composition, and has (or is converted to have) the same unit of measurement as M. As a result, C/M is a unitless value. By way of example, if a perfume raw material is present in a perfume accord in an amount of 1.00 wt. %, the perfume accord is present in the shampoo composition in an amount of 0.8%, and M is in ppm, the value of C for the perfume raw material is calculated as follows:

$$(1.00/100)*(0.8/100)*10^6 = 80 \text{ ppm}.$$

Further, if the value for M in this example is 500 ppm, the value of C/M is 80 ppm/500 ppm=0.16.

Table 2 lists the wt. % of each perfume raw material in perfume accord 2A, M for each perfume raw material in shampoo composition II, and C/M for each perfume raw material when 0.8% perfume accord 2A is present in the shampoo composition.

TABLE 2

| Perfume Accord 2A | | | |
|---|---|---|---|
| Material Name | Wt. % | M (ppm) | C/M |
| Undecalactone | 22.00 | 583 | 3.02 |
| Cis 3 Hexenyl Acetate | 0.75 | 61 | 0.99 |

TABLE 2-continued

| Perfume Accord 2A | | | |
|---|---|---|---|
| Material Name | Wt. % | M (ppm) | C/M |
| Delta Damascone | 0.80 | 117 | 0.55 |
| Cymal | 1.00 | 1654 | 0.05 |
| Methyl Phenyl Carbinyl Acetate | 1.00 | 433 | 0.18 |
| Nerolidol | 1.00 | 546 | 0.15 |
| Musk Plus | 2.00 | 4481 | 0.04 |
| Galaxolide | 7.00 | 6448 | 0.09 |
| Allyl Cyclohexane Propionate | 2.80 | 725 | 0.31 |
| Hexyl Salicylate | 22.00 | 8466 | 0.21 |
| Linalool | 12.50 | 389 | 2.57 |
| Ligustral Or Triplal | 0.20 | 86 | 0.19 |
| Dimethyl Benzyl Carbinyl Butyrate | 3.50 | 1969 | 0.14 |
| Helional | 1.80 | 7345 | 0.02 |
| P.t.bucinal | 15.00 | 1727 | 0.69 |
| Dimethyl Benzyl Carbinyl Acetate | 1.80 | 1270 | 0.11 |
| Hexyl Acetate | 1.00 | 180 | 0.44 |
| Ethyl-2-methyl Butyrate | 1.00 | 37 | 2.14 |
| Methyl Dihydro Jasmonate | 2.00 | 6478 | 0.02 |
| Dipropylene Glycol | 0.85 | 17414 | 0.00 |

Perfume accord 2A demonstrates an odor intensity score (OIS) in shampoo composition II of 0.60, as obtained by summing all C/M values in the table and dividing by the total number of perfume raw materials.

Table 3 lists the wt. % of each perfume raw material in perfume accord 2B, M for each perfume raw material in shampoo composition I, and C/M for each perfume raw material when 0.8% perfume accord 2B is present in the shampoo composition.

TABLE 3

| Perfume Accord 2B | | | |
|---|---|---|---|
| Material Name | Wt. % | M (ppm) | C/M |
| Allyl Heptoate | 3.50 | 193.4 | 1.45 |
| Alpha Damascone | 0.20 | 229.5 | 0.07 |

TABLE 3-continued

Perfume Accord 2B

| Material Name | Wt. % | M (ppm) | C/M |
|---|---|---|---|
| Terpineol | 0.50 | 1386.9 | 0.03 |
| Ambroxan | 0.35 | 566.4 | 0.05 |
| Beta Gamma Hexenol | 0.50 | 541.0 | 0.07 |
| Cedryl Methyl Ether | 4.50 | 2791.3 | 0.13 |
| Citral | 0.50 | 123.1 | 0.32 |
| Cyclemax | 2.20 | 316.1 | 0.56 |
| Cyclo Galbanate | 0.20 | 351.4 | 0.05 |
| Ethyl Linalool | 6.80 | 468.7 | 1.16 |
| Galaxolide | 10.00 | 8160.6 | 0.10 |
| Geraniol | 0.50 | 416.8 | 0.10 |
| Geranyl Acetate | 0.50 | 4145.2 | 0.01 |
| d-limonene | 10.00 | 385.0 | 2.08 |
| Iso Cyclo Citral | 0.05 | 103.7 | 0.04 |
| Iso E Super Or Wood | 8.00 | 512.0 | 1.25 |
| Liffarome | 0.50 | 206.0 | 0.19 |
| Ethyl 2 Methyl Pentanoate | 0.50 | 81.1 | 0.49 |
| Methyl Dihydro Jasmonate | 7.50 | 7990.3 | 0.08 |
| Galaxolide | 7.50 | 8160.6 | 0.07 |
| Neryl Acetate | 0.20 | 1568.0 | 0.01 |
| P.t.bucinal | 10.00 | 2034.5 | 0.39 |
| Phenyl Ethyl Iso Butyrate | 0.50 | 621.0 | 0.06 |
| Rosemary | 0.20 | 4137.6 | 0.00 |
| Timberol | 2.20 | 1862.2 | 0.09 |
| Ligustral | 0.70 | 96.2 | 0.58 |
| Undecalactone | 6.90 | 677.7 | 0.81 |
| Undecylenic Aldehyde | 0.20 | 99.2 | 0.16 |
| Verdox | 5.70 | 1287.5 | 0.35 |
| Jasmolactone | 0.10 | 2034.4 | 0.00 |
| Hexyl Salicylate | 5.50 | 9979.7 | 0.04 |
| Linalool | 3.50 | 463.6 | 0.60 |

Perfume accord 2B demonstrates an odor intensity score (OIS) in shampoo composition I of 0.36, as obtained by summing all C/M values in the table and dividing by the total number of perfume raw materials.

Table 4 lists the wt. % of each perfume raw material in perfume accord 2C, M for each perfume raw material in shampoo composition I, and C/M for each perfume raw material when 0.8% perfume accord 2C is present in the shampoo composition.

TABLE 4

Perfume Accord 2C

| Material Name | Wt. % | M (ppm) | C/M |
|---|---|---|---|
| Dodecyl acetate | 1.64 | 51.2 | 2.55 |
| Cis 3 Hexenyl Acetate | 0.32 | 60.6 | 0.42 |
| Ligustral Or Triplal | 0.62 | 86.1 | 0.58 |
| Lauric Aldehyde | 0.18 | 136.6 | 0.11 |
| Hexyl Acetate | 3.17 | 180.2 | 1.41 |
| Liffarome | 0.12 | 185.6 | 0.05 |
| Allyl Amyl Glycolate | 0.27 | 177.0 | 0.12 |
| Nonalactone | 3.37 | 192.1 | 1.40 |
| Ionone Gamma Methyl | 3.07 | 155.7 | 1.58 |
| Methyl Pamplemousse | 0.13 | 239.9 | 0.04 |
| Eugenol | 0.26 | 261.7 | 0.08 |
| Orange Terpenes | 4.41 | 354.4 | 1.00 |
| Cis 3 Hexenyl Butyrate | 0.15 | 345.1 | 0.04 |
| Flor Acetate | 3.84 | 319.5 | 0.96 |
| Cashmeran | 2.61 | 320.8 | 0.65 |
| Linalool | 5.96 | 388.6 | 1.23 |
| Ethyl Linalool | 3.70 | 389.8 | 0.76 |
| Methyl Phenyl Carbinyl Acetate | 2.82 | 433.2 | 0.52 |
| Iso E Super Or Wood | 18.44 | 410.9 | 3.59 |
| Undecalactone | 1.20 | 582.7 | 0.16 |
| Floralozone | 0.35 | 631.4 | 0.04 |
| Dihydro Myrcenol | 5.45 | 644.4 | 0.68 |
| Verdox | 4.11 | 1103.7 | 0.30 |
| Adoxal | 0.18 | 1227.6 | 0.01 |
| Dimethyl Benzyl Carbinyl Acetate | 0.91 | 1270.0 | 0.06 |
| Diphenyl Oxide | 0.04 | 1382.7 | 0.00 |

TABLE 4-continued

Perfume Accord 2C

| Material Name | Wt. % | M (ppm) | C/M |
|---|---|---|---|
| P.T.Bucinal | 5.56 | 1726.7 | 0.26 |
| Cedryl Methyl Ether | 2.76 | 2243.6 | 0.10 |
| Coumarin | 0.15 | 3423.2 | 0.00 |
| Diethylphthalate | 1.10 | 5040.2 | 0.02 |
| Methyl Dihydro Jasmonate | 14.85 | 6477.7 | 0.18 |
| Ethyl Trimethylcyclopentene Butenol | 1.41 | 8470.5 | 0.01 |
| Patchouli Oil Md 24117 - Daniel | 0.08 | 1193.9 | 0.01 |
| Spearmint oil | 0.20 | 88.7 | 0.18 |
| Italian Mandarin Oil Yellow #10567 | 0.67 | 1730.1 | 0.03 |
| Galbanum Oil LMR | 0.26 | 431.9 | 0.05 |
| Sweet Orange Oil Tarocco Decol. #10977 | 2.81 | 354.4 | 0.63 |
| Cedarwood Texas Light | 0.16 | 1858.8 | 0.01 |
| Rosemary | 2.48 | 3607.8 | 0.05 |
| OLIBANUM RESIN. 70/30 W/O APE(CONF. CHAUV) | 0.20 | 1215.6 | 0.01 |

Perfume accord 2C demonstrates an odor intensity score (OIS) in shampoo composition I of 0.50, as obtained by summing all C/M values in the table and dividing by the total number of perfume raw materials.

Example 3

Shampoo Compositions Comprising Efficient Perfume Accords

Perfume compositions in accordance with the invention were prepared according to the formulations provided in Tables 5 to 6. The amount of perfume raw material provided in the table is a percent by weight (wt. %) based on the total weight of the perfume accord (i.e., the blend of perfume raw materials).

Table 5 lists the wt. % of each perfume raw material in perfume accord 3A, M for each perfume raw material in shampoo composition II, and C/M for each perfume raw material when 0.2% perfume accord 3A is present in the shampoo composition.

TABLE 5

Perfume Accord 3A

| Material Name | Wt. % | M (ppm) | C/M |
|---|---|---|---|
| Octyl Aldehyde | 0.33 | 101.8 | 0.06 |
| Oxane | 0.44 | 8.3 | 1.06 |
| Pino Acetaldehyde | 0.81 | 133.7 | 0.12 |
| Anethol Usp | 0.87 | 343.1 | 0.05 |
| Alpha Damascone | 1.24 | 193.5 | 0.13 |
| Citronellol | 1.25 | 726.7 | 0.03 |
| Methyl Pamplemousse | 1.47 | 239.9 | 0.12 |
| Ambronat | 1.61 | 150.4 | 0.21 |
| 4 - Tertiary Butyl Cyclohexyl Acetate | 2.26 | 219.6 | 0.21 |
| Hexyl Acetate | 2.34 | 180.2 | 0.26 |
| Cis 3 Hexenyl Acetate | 2.48 | 60.6 | 0.82 |
| Melonal | 2.71 | 36.6 | 1.48 |
| Irone Alpha Refined | 2.75 | 147.6 | 0.37 |
| Dimethyl Benzyl Carbinyl Acetate | 3.10 | 1270.0 | 0.05 |
| Precyclemone B | 3.49 | 1943.2 | 0.04 |
| Frutene | 3.61 | 169.6 | 0.43 |
| Helvetolide 947650 | 3.64 | 1225.6 | 0.06 |
| Undecalactone | 3.70 | 582.7 | 0.13 |
| Ethyl 2 Methyl Pentanoate | 4.72 | 73.8 | 1.28 |
| Phenyl Acetaldehyde | 5.28 | 61.6 | 1.71 |
| Gamma Decalactone | 5.56 | 1068.2 | 0.10 |
| Dihydro Beta Ionone | 5.29 | 249.5 | 0.42 |
| Ethyl-2-Methyl Butyrate | 6.26 | 37.4 | 3.34 |
| Ethyl Methyl Phenyl Glycidate | 8.22 | 1184.5 | 0.14 |

TABLE 5-continued

Perfume Accord 3A

| Material Name | Wt. % | M (ppm) | C/M |
|---|---|---|---|
| Romascone | 8.44 | 157.4 | 1.07 |
| Citral | 8.94 | 106.7 | 1.68 |
| Ethyl Vanillin | 9.22 | 56.9 | 3.24 |

Perfume accord 3A demonstrates an odor intensity score (OIS) in shampoo composition II of 0.69, as obtained by summing all C/M values in the table and dividing by the total number of perfume raw materials. Therefore, an efficient composition comprising perfume accord 3A demonstrated a similar OIS at a significantly lower concentration relative to the comparative compositions comprising perfume accords 2A, 2B, and 2C (OIS=0.69 vs. 0.60, 0.36, and 0.50; concentration=0.2 wt. % vs. 0.8 wt. %) (see Example 2).

Table 6 lists the wt. % of each perfume raw material in perfume accord 3B, M for each perfume raw material in shampoo composition II, and C/M for each perfume raw material when 0.8% perfume accord 3B is present in the shampoo composition.

TABLE 6

Perfume Accord 3B

| Material Name | Wt. % | M (ppm) | C/M |
|---|---|---|---|
| Ligustral Or Triplal | 0.80 | 185.0 | 0.35 |
| Cis 3 Hexenyl Acetate | 1.20 | 60.6 | 1.58 |
| Delta Damascone | 1.20 | 116.7 | 0.82 |
| Cyclemax | 8.00 | 274.3 | 2.33 |
| Ethyl-2-methyl Butyrate | 1.00 | 37.4 | 2.14 |
| Hexyl Acetate | 8.00 | 180.2 | 3.55 |
| Allyl Cyclohexane Propionate | 13.00 | 725.1 | 1.43 |
| Ethyl Linalool | 16.00 | 389.8 | 3.28 |
| Undecalactone | 20.00 | 582.7 | 2.75 |
| Ambroxan | 1.00 | 451.1 | 0.18 |
| Florhydral | 4.00 | 520.2 | 0.62 |
| Ethyl 2 Methyl Pentanoate | 5.00 | 73.8 | 5.42 |
| Prenyl Acetate | 1.00 | 37.1 | 2.16 |
| Ethyl Maltol | 0.20 | 16299.5 | 0.00 |
| Methyl Iso Butenyl Tetrahydro Pyran | 0.20 | 153.3 | 0.10 |
| Ethyl Oenanthate | 4.00 | 202.4 | 1.58 |
| Oxane | 0.40 | 8.3 | 3.84 |
| Allyl Heptoate | 8.00 | 172.4 | 3.71 |
| Frutene | 3.00 | 169.6 | 1.41 |
| Ionone Gamma Methyl | 4.00 | 155.7 | 2.06 |

Perfume accord 3B demonstrates an odor intensity score (OIS) in shampoo composition II of 1.97, as obtained by summing all C/M values in the table and dividing by the total number of perfume raw materials. Therefore, an efficient composition comprising perfume accord 3B demonstrated a significantly higher OIS relative to the comparative compositions comprising perfume accords 2A, 2B, and 2C (OIS=1.97 vs. 0.60, 0.36, and 0.50) (see Example 2) when present at the same concentration as perfume accords 2A, 2B, and 2C (0.8 wt. %).

Example 4

Preparation of Body Wash Compositions

Body wash composition I was prepared by conventional formulation and mixing techniques. The component amounts provided in Table 7 are percent by weight (wt. %) based on the total weight of the body wash composition.

TABLE 7

| Ingredient | EXAMPLE BODY WASH COMPOSITION I |
|---|---|
| Water | q.s. |
| Sodium Laureth Sulfate | 7.5 |
| Cocomidopropyl Betaine | 1.5 |
| Sodium Chloride | 1.6 |
| Methyl Chloro Isothiazolinone | 0.033 |
| Citric Acid | 0.17 |
| Sodium Benzoate | 0.25 |
| Disodium EDTA | 0.1 |

Example 5

Body Wash Compositions Comprising Comparative Perfume Accords

Comparative perfume compositions were prepared according to the formulations provided in Tables 8 to 10. The amount of perfume raw material provided in the table is a percent by weight (wt. %) based on the total weight of the perfume accord (i.e., the blend of perfume raw materials).

M is the concentration of the perfume raw material sufficient to provide an odor intensity rating (OIR) in body wash composition I of about 2 on a scale from zero to five. C is the concentration of the perfume raw material in the body wash composition, and has (or is converted to have) the same unit of measurement as M. As a result, C/M is a unitless value. By way of example, if a perfume raw material is present in a perfume accord in an amount of 1.00 wt. %, the perfume accord is present in the body wash composition in an amount of 0.8%, and M is in ppm, the value of C for the perfume raw material is calculated as follows:

$$(1.00/100)*(0.8/100)*10^6 = 80 \text{ ppm}.$$

Further, if the value for M in this example is 500 ppm, the value of C/M is 80 ppm/500 ppm=0.16.

Table 8 lists the wt. % of each perfume raw material in perfume accord 8A, M for each perfume raw material in body wash composition I, and C/M for each perfume raw material when 1.5% perfume accord 8A is present in the body wash composition.

TABLE 8

Perfume Accord 8A

| Material Name | Wt. % | M (ppm) | C/M |
|---|---|---|---|
| Ambrofix | 0.50 | 72.5 | 1.03 |
| Linalyl Acetate | 3.00 | 564.0 | 0.80 |
| Beta Gamma Hexenol | 0.20 | 347.5 | 0.09 |
| Oxane | 0.5 | 5.3 | 0.57 |
| Cis 3 Hexenyl Acetate | 0.75 | 39.5 | 2.85 |
| Ambrettolide | 1.00 | 3341.3 | 0.04 |
| Cis Jasmone | 0.40 | 1888.6 | 0.03 |
| Cis-3-Hexenyl Benzoate | 0.10 | 16.6 | 0.90 |
| Hexyl Salicylate | 4.00 | 6298.9 | 0.10 |
| Linalool | 3.00 | 278.3 | 1.62 |
| Cyclo Galbanate | 0.10 | 188.4 | 0.08 |
| Delta Damascone | 0.15 | 74.5 | 0.30 |
| Dihydro Myrcenol | 4.00 | 433.3 | 1.38 |
| Ethyl Caproate | 0.15 | 43.2 | 0.52 |
| Ethyl-2-Methyl Butyrate | 0.50 | 25.0 | 3.00 |
| Floralozone | 1.00 | 346.3 | 0.43 |
| Hexamethylindanopyran | 10.00 | 3317.3 | 0.45 |
| Helional | 2.50 | 5214.0 | 0.07 |
| Heliotropin | 0.20 | 165.0 | 0.18 |
| Hexyl Acetate | 0.30 | 120.4 | 0.37 |

TABLE 8-continued

Perfume Accord 8A

| Material Name | Wt. % | M (ppm) | C/M |
|---|---|---|---|
| Hexyl Cinnamic Aldehyde | 8.00 | 3403.5 | 0.35 |
| Ionone Beta | 1.94 | 110.1 | 2.64 |
| Ionone Gamma Methyl | 5.00 | 100.6 | 7.46 |
| Iso E Super Or Wood | 7.00 | 231.5 | 4.54 |
| Iso Eugenol | 0.20 | 164.0 | 0.18 |
| Iso Eugenol Acetate | 0.20 | 6900.3 | 0.00 |
| Lemon Cold-Pressed | 2.50 | 215.6 | 1.74 |
| Lrg 201 | 0.10 | 7551.4 | 0.00 |
| Lyral | 7.00 | 5797.5 | 0.18 |
| Melonal | 0.40 | 24.9 | 2.41 |
| Methyl Dihydro Jasmonate | 15.41 | 3875.8 | 0.60 |
| Para Hydroxy Phenyl Butanone | 0.50 | 1631.8 | 0.23 |
| Phenoxanol | 5.00 | 2659.5 | 0.28 |
| Phenoxy Ethyl Iso Butyrate | 4.00 | 8779.9 | 0.08 |
| Polysantol | 0.75 | 3276.9 | 0.03 |
| SANJINOL | 3.00 | 5555.9 | 0.08 |
| Undecalactone | 0.60 | 458.1 | 0.20 |
| Undecavertol | 2.50 | 264.5 | 1.42 |
| Gamma Decalactone | 0.08 | 837.5 | 0.01 |
| Indolene | 0.01 | 4309979.7 | 0.00 |
| Ethyl Maltol | 0.01 | 9583.5 | 0.00 |
| Dipropylene Glycol | 1.12 | 10623.0 | 0.02 |

Perfume accord 8A demonstrates an odor intensity score (OIS) in body wash composition I of 0.89, as obtained by summing all C/M values in the table and dividing by the total number of perfume raw materials.

Table 9 lists the wt. % of each perfume raw material in perfume accord 8B, M for each perfume raw material in body wash composition I, and C/M for each perfume raw material when 1.5% perfume accord 8B is present in the body wash composition.

TABLE 9

Perfume Accord 8B

| Material Name | Wt. % | M (ppm) | C/M |
|---|---|---|---|
| Dodecyl acetate | 0.22 | 35.2 | 0.95 |
| Ethyl 2 Methyl Pentanoate | 0.05 | 49.0 | 0.15 |
| Methyl Nonyl Ketone | 0.02 | 49.5 | 0.05 |
| Delta Damascone | 0.05 | 74.5 | 0.10 |
| Lauric Aldehyde | 0.14 | 96.9 | 0.22 |
| Ambronat | 0.14 | 72.5 | 0.30 |
| Hexyl Acetate | 0.07 | 120.4 | 0.09 |
| Allyl Amyl Glycolate | 0.40 | 113.4 | 0.53 |
| Alpha Damascone | 0.14 | 112.7 | 0.19 |
| Ionone Gamma Methyl | 0.97 | 119.1 | 1.21 |
| 4 - Tertiary Butyl Cyclohexyl Acetate | 3.32 | 138.7 | 3.59 |
| Orange Oil Cold Pressed | 6.94 | 215.6 | 4.83 |
| Geraniol | 1.63 | 245.5 | 1.00 |
| Linalool | 7.25 | 278.3 | 3.91 |
| Benzyl Acetate | 2.10 | 296.7 | 1.06 |
| Iso E Super Or Wood | 8.71 | 231.5 | 5.65 |
| Dihydro Myrcenol | 11.93 | 433.3 | 4.13 |
| Allyl Cyclohexane Propionate | 0.06 | 460.1 | 0.02 |
| Linalyl Acetate | 1.41 | 564.0 | 0.38 |
| Verdox | 1.83 | 697.3 | 0.39 |
| ALPHA TERPINEOL | 0.99 | 782.1 | 0.19 |
| Terpinyl Acetate | 3.87 | 901.0 | 0.64 |
| Cymal | 1.31 | 1156.8 | 0.17 |
| P.T.Bucinal | 10.85 | 1191.2 | 1.37 |
| Amyl Salicylate | 2.22 | 1412.7 | 0.24 |
| Cedryl Methyl Ether | 1.75 | 1011.3 | 0.26 |
| Boisambrene Forte (S 506) | 0.92 | 1664.8 | 0.08 |
| Hexyl Cinnamic Aldehyde | 0.37 | 3403.5 | 0.02 |
| Hexamethylindanopyran | 15.69 | 3317.6 | 0.71 |
| Methyl Dihydro Jasmonate | 3.49 | 3875.8 | 0.14 |
| Helional | 2.50 | 5214.0 | 0.07 |
| Hexyl Salicylate | 1.59 | 6298.9 | 0.04 |
| Ethyl Trimethylcyclopentene Butenol | 0.53 | 5555.9 | 0.01 |
| Ethylene Brassylate | 0.37 | 8003.7 | 0.01 |

TABLE 9-continued

Perfume Accord 8B

| Material Name | Wt. % | M (ppm) | C/M |
|---|---|---|---|
| Benzyl Salicylate | 2.50 | 15675.6 | 0.02 |
| Butylated Hydroxy Toluene | 0.03 | 271641.9 | 0.00 |
| Cedarwood Texas Light | 0.79 | 999.1 | 0.12 |
| Lavender | 2.17 | 278.3 | 1.17 |
| Oil Lime Expressed Mex Fcc 150421 | 0.66 | 215.6 | 0.46 |
| Geranium bourbon G109 29196 | 0.06 | 245.5 | 0.03 |

Perfume accord 8B demonstrates an odor intensity score (OIS) in body wash composition I of 0.86, as obtained by summing all C/M values in the table and dividing by the total number of perfume raw materials.

Example 6

Body Wash Composition Comprising an Efficient Perfume Accord

Perfume compositions in accordance with the invention were prepared according to the formulations provided in Tables 10 and 11. The amount of perfume raw material provided in the table is a percent by weight (wt. %) based on the total weight of the perfume accord (i.e., the blend of perfume raw materials).

Table 10 lists the wt. % of each perfume raw material in perfume accord 9A, M for each perfume raw material in body wash composition I, and C/M for each perfume raw material when 0.35% perfume accord 9A is present in the body wash composition.

TABLE 10

Perfume Accord 9A

| Material Name | Wt. % | M (ppm) | C/M |
|---|---|---|---|
| Octyl Aldehyde | 0.33 | 73.0 | 0.16 |
| Oxane | 0.44 | 5.3 | 2.92 |
| Pino Acetaldehyde | 0.81 | 85.8 | 0.33 |
| Anethol Usp | 0.87 | 239.9 | 0.13 |
| Alpha Damascone | 1.24 | 112.7 | 0.39 |
| Citronellol | 1.25 | 522.4 | 0.08 |
| Methyl Pamplemousse | 1.47 | 137.9 | 0.37 |
| Ambronat | 1.61 | 72.5 | 0.78 |
| 4 - Tertiary Butyl Cyclohexyl Acetate | 2.259 | 138.7 | 0.57 |
| Hexyl Acetate | 2.339 | 120.4 | 0.68 |
| Cis 3 Hexenyl Acetate | 2.479 | 39.5 | 2.20 |
| Melonal | 2.709 | 24.9 | 3.81 |
| Irone Alpha Refined | 2.749 | 93.2 | 1.03 |
| Dimethyl Benzyl Carbinyl Acetate | 3.099 | 859.8 | 0.13 |
| Precyclemone B | 3.489 | 1280.8 | 0.10 |
| Frutene | 3.609 | 89.1 | 1.42 |
| Helvetolide 947650 | 3.639 | 680.4 | 0.19 |
| Undecalactone | 3.699 | 458.1 | 0.28 |
| Ethyl 2 Methyl Pentanoate | 4.719 | 49.0 | 3.37 |
| Phenyl Acetaldehyde | 5.278 | 46.9 | 3.94 |
| Gamma Decalactone | 5.558 | 837.5 | 0.23 |
| Dihydro Beta Ionone | 5.288 | 155.2 | 1.19 |
| Ethyl-2-Methyl Butyrate | 6.258 | 25.0 | 8.77 |
| Ethyl Methyl Phenyl Glycidate | 8.218 | 836.6 | 0.34 |
| Romascone | 8.437 | 103.0 | 2.87 |
| Citral | 8.937 | 73.5 | 4.26 |
| Ethyl Vanillin | 9.217 | 50.5 | 6.39 |

Perfume accord 9A demonstrates an odor intensity score (OIS) in body wash composition I of 1.74, as obtained by summing all C/M values in the table and dividing by the total number of perfume raw materials. Therefore, an efficient composition comprising perfume accord 9A demonstrated a similar OIS at a significantly lower concentration relative to the comparative compositions comprising perfume accords 8A and 8B (OIS=1.74 vs. 0.89 and 0.86; concentration=0.35 wt. % vs. 1.5 wt. %) (see Example 5).

Table 11 lists the wt. % of each perfume raw material in perfume accord 9B, M for each perfume raw material in body wash composition I, and C/M for each perfume raw material when 1.5% perfume accord 9B is present in the body wash composition.

TABLE 11

Perfume Accord 9B

| Material Name | Wt. % | M (ppm) | C/M |
|---|---|---|---|
| Lemon Cold-Pressed | 4.44 | 215.6 | 3.08 |
| Melonal | 1.48 | 24.9 | 8.91 |
| Para Hydroxy Phenyl Butanone | 4.44 | 1631.8 | 0.59 |
| Undecalactone | 4.44 | 458.1 | 1.45 |
| Ligustral Or Triplal | 0.59 | 59.4 | 1.49 |
| Undecavertol | 4.44 | 264.5 | 2.52 |
| Iso E Super Or Wood | 29.56 | 231.5 | 20.58 |
| Iso Eugenol | 0.59 | 164.0 | 0.54 |
| Ambronat | 0.74 | 72.5 | 1.53 |
| Beta Gamma Hexenol | 0.30 | 347.5 | 0.13 |
| Ethyl Maltol | 2.96 | 9583.5 | 0.02 |
| Oxane | 1.48 | 5.3 | 0.57 |
| Cis 3 Hexenyl Acetate | 1.11 | 39.5 | 4.21 |
| Delta Damascone | 0.74 | 74.5 | 1.49 |
| Dihydro Myrcenol | 4.44 | 433.3 | 1.54 |
| Ethyl Caproate | 2.96 | 43.2 | 10.27 |
| Ethyl-2-Methyl Butyrate | 1.48 | 25.0 | 8.87 |
| Heliotropin | 0.59 | 165.0 | 0.54 |
| Hexyl Acetate | 7.39 | 120.4 | 9.21 |
| Ionone Gamma Methyl | 10.35 | 100.6 | 15.44 |
| Linalool | 10.35 | 278.3 | 5.58 |
| Linalyl Acetate | 4.44 | 564.0 | 1.18 |

Perfume accord 9B demonstrates an odor intensity score (OIS) in body wash composition I of 4.53, as obtained by summing all C/M values in the table and dividing by the total number of perfume raw materials. Therefore, an efficient composition comprising perfume accord 9B demonstrated a significantly higher OIS relative to the comparative compositions comprising perfume accords 8A and 8B (OIS=4.53 vs. 0.89 and 0.86) (see Example 8) when present at the same concentration as perfume accords 8A and 8B (1.5 wt. %).

Example 7

Preparation of a Lipid-Containing Body Wash Composition

A lipid-containing body wash composition (body wash composition II) was prepared by the following procedure. The component amounts provided in Table 12 are percent by weight (wt. %) based on the total weight of the structured surfactant phase composition or by weight (wt. %) based on the total weight of the oil continuous benefit phase composition.

A citric acid solution was prepared by adding citric acid and distilled water into a first mixing vessel at a ratio of 50:50. In a second mixing vessel containing water, guar hydroxypropyltrimonium chloride polymer was added with agitation. Sodium lauroamphoacetate, sodium lauryl sulfate, sodium trideceth sulfate, trideceth-3, xanthan gum, polyethylene glycol, sodium chloride, EDTA, sodium benzoate, and Expancel were added to the second mixing vessel. The pH of the mixture in the second mixing vessel was adjusted to 5.7±0.2 using the citric acid solution. Perfume and methyl chloro isothiazolinone and methyl isothiazolinone were added to the second mixing vessel and mixed until homogeneous, thereby forming a structured surfactant phase.

The oil continuous benefit phase was prepared by adding petrolatum into a third mixing vessel while heating the third mixing vessel to about 88° C. Mineral oil was added to the third mixing vessel with mixing. Titanium dioxide was added to the third mixing vessel with adequate mixing. The mixture in the third mixing vessel was then cooled to 45° C. with agitation. At 45° C., the agitation was stopped and the mixture in the third mixing vessel was cooled to room temperature. The oil continuous benefit phase was blended with the structured surfactant phase at a specified ratio (90:10 w/w structured surfactant phase:oil benefit phase) using a SpeedMixer™ (from FlackTek Inc.) at 2800 rpm for 1 min.

TABLE 12

| Ingredient | Composition wt. % |
|---|---|
| I: Structured surfactant phase composition | |
| sodium trideceth sulfate, sulfated to >95% from ICONOL ™ TDA-3 tridecyl alcohol alkoxylate (BASF Corp.) | 7.23 |
| sodium lauryl sulfate (Procter & Gamble) | 7.23 |
| sodium lauroamphoacetate (Cognis Corp.) | 4.25 |
| guar hydroxypropyltrimonium chloride N-HANCE ® 3196 from Aqualon) | 0.51 |
| sodium chloride | 4.75 |
| trideceth-3 (ICONOL ™ TDA-3I from BASF Corp.) | 1.7 |
| Expancel (091 WE40 d24 from AlzoNobel) | 2 |
| polyethylene glycol (POLYOX ™ WSR-301 from Dow Chemical) | 0.13 |
| xanthan gum (KELTROL ®l 1000 from CP Kelco) | 0.19 |
| methyl chloro isothiazolinone and methyl isothiazolinone (KATHON ™ CG from Rohm & Haas) | 0.028 |
| Ethylenediaminetetraacetic acid (DISSOLVINE NA 2x from Akzo Nobel) | 0.13 |
| sodium benzoate | 0.17 |
| perfume | 1.5 |
| citric acid, titrated to a pH of | 5.7 ± 0.2 |
| water and minors | Q.S. |
| II: Oil continuous benefit phase composition | |
| Petrolatum (G2218 from Sonnerbonn) | 56 |
| Mineral Oil (Hydrobrite 1000 White Mineral Oil from Sonnerbonn) | 24 |
| titanium oxide, silane coated (RBTD-834-11S2 from Kobo Products) | 20 |
| III: Blending Ratio of Structured Surfactant Phase:Oil Benefit Phase | 90:10 |

Example 8

Sensory Response to Perfume Accords

The sensory intensity of a comparative perfume accord and of an efficient perfume accord (i.e., a perfume accord according to the invention) present at 1.5 wt. % in a lipid-containing body wash was determined on a scale from 0 to 8 using a sensory panel. The sensory panel consisted of 15 to 20 naïve panelists, both male and female, aged 25 to 55. An individual rating by a panel member of zero means that the individual could not detect an odor and an individual rating by a panel member of 8 means that the individual could detect an extremely strong odor. The ratings of each panel member were summed and divided by the number of members to provide a mean sensory intensity score.

The mean sensory intensity score for perfume accords 8A and 9B are provided in Table 13. Table 13 demonstrates that a body wash composition with an efficient perfume accord (i.e., a perfume accord in accordance with the invention), such as perfume accord 9B, has a significantly increased mean sensory intensity score compared to a perfume accord not in accordance with the invention, such as perfume accord 8A.

TABLE 13

| Perfume Accord | OIS | Mean Sensory Intensity Score |
| --- | --- | --- |
| 8A | 0.21 | 4.2 |
| 9B | 1.05 | 5.3 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of making a body wash composition comprising:
    adding about 3 wt. % to about 15 wt. %, based on the total weight of the body wash composition, of anionic surfactants; and
    adding about 0.05 wt. % to about 0.4 wt. %, based on the total weight of the body wash composition, of a perfume accord comprising at least 10 perfume raw materials, and
    determining that the body wash composition has an odor intensity score (OIS) of at least about 0.8, as determined by Formula I:

$$1/n \sum_{i=1}^{n} C_i / M_i = OIS \qquad \text{Formula (I)}$$

wherein n is the number of perfume raw materials present in the perfume accord, $C_i$ is the concentration of the $i^{th}$ perfume raw material in the body wash composition, and $M_i$ is the concentration of the $i^{th}$ perfume raw material sufficient to provide an odor intensity rating (OIR) in a body wash composition chassis of about 2 on a scale from zero to five, wherein the body wash composition chassis is the body wash composition without the perfume accord.

2. The method of making a body wash composition of claim 1, wherein the OIS is about 0.8 to about 2.

3. A method of making a body wash composition comprising:
    adding about 3 weight % (wt. %) to about 15 wt. %, based on the total weight of the body wash composition, of anionic surfactants; and
    adding about 0.4 wt. % to about 1.5 wt. %, based on the total weight of the body wash composition, of a perfume accord comprising at least 10 perfume raw materials,
    determining that the body wash composition has an odor intensity score (OIS) of at least about 1, as determined by Formula I:

$$1/n \sum_{i=1}^{n} C_i / M_i = OIS \qquad \text{Formula (I)}$$

wherein n is the number of perfume raw materials present in the perfume accord, $C_i$ is the concentration of the $i^{th}$ perfume raw material in the body wash composition, and $M_i$ is the concentration of the $i^{th}$ perfume raw material sufficient to provide an odor intensity rating (OIR) in a body wash composition chassis of about 2 on a scale from zero to five, wherein the body wash composition chassis is the body wash composition without the perfume accord.

4. The method of making a body wash composition of claim 3, wherein the OIS is about 1 to about 11.

5. The method of claim 3, wherein $M_i$ is about 1 ppm to about 1000 ppm for about 20% to about 100% of the perfume raw materials present in the perfume accord.

6. The method of claim 5, wherein $M_i$ is about 1 ppm to about 800 ppm.

7. The method of claim 6, wherein $M_i$ is about 1 ppm to about 600 ppm.

8. The method of claim 3, wherein $C_i/M_i$ is at least 0.05 for about 75% to about 100% of the perfume raw materials present in the perfume accord.

9. The method of claim 3, wherein $C_i/M_i$ is at least 0.1 for about 70% to about 100% of the perfume raw materials present in the perfume accord.

10. The method of claim 3, wherein $C_i/M_i$ is at least 0.2 for about 45% to about 100% of the perfume raw materials present in the perfume accord.

11. The method of claim 3, wherein $C_i/M_i$ is at least 0.3 for about 40% to about 100% of the perfume raw materials present in the perfume accord.

12. The method of claim 3, wherein $C_i/M_i$ is at least 0.4 for about 35% to about 100% of the perfume raw materials present in the perfume accord.

13. The method of claim 3, wherein $C_i/M_i$ is at least 0.5 for about 30% to about 100% of the perfume raw materials present in the perfume accord.

14. The method of claim 3, wherein $C_i/M_i$ is at least 0.6 for about 25% to about 100% of the perfume raw materials present in the perfume accord.

15. The method of claim 3, wherein $C_i/M_i$ is at least 0.7 for about 20% to about 100% of the perfume raw materials present in the perfume accord.

16. The method of claim 15, wherein $C_i/M_i$ is at least 0.8.

17. The method of claim 15, wherein $C_i/M_i$ is at least 0.9.

18. The method of claim 3, wherein $C_i/M_i$ is at least 1 for about 15% to about 100% of the perfume raw materials in the perfume accord.

19. The method of claim 3, wherein the perfume raw materials are selected from the group consisting of 2-Nonen- 1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

20. The method of claim 3, wherein the anionic surfactants are selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium trideceth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, branched and non-branched versions of decyl and undecyl alkyl sulfates which are either ethoxylated or non-ethoxylated; decyl alcohol modified lauryl sulfate; paraffin sulfonates with chain lengths ranging from C13 to C17; mixtures of linear and branched-chain alcohol sulfates with carbon chain lengths C12 to C17 which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates, and mixtures thereof.

* * * * *